United States Patent
Govari et al.

(10) Patent No.: US 7,860,553 B2
(45) Date of Patent: Dec. 28, 2010

(54) TWO-STAGE CALIBRATION OF MEDICAL PROBES

(75) Inventors: Assaf Govari, Haifa (IL); Dmitri Model, Haifa (IL); Yaron Ephrath, Karkur (IL); Andres Claudio Altmann, Haifa (IL)

(73) Assignee: Biosense Webster, Inc., Diamond Bar, CA (US)

( * ) Notice: Subject to any disclaimer, the term of this patent is extended or adjusted under 35 U.S.C. 154(b) by 197 days.

(21) Appl. No.: 11/351,135

(22) Filed: Feb. 9, 2006

(65) Prior Publication Data

US 2007/0185397 A1 Aug. 9, 2007

(51) Int. Cl.
*A61B 5/05* (2006.01)

(52) U.S. Cl. ................. 600/424; 600/429; 600/431; 600/434; 702/85; 702/93

(58) Field of Classification Search ............... 600/300, 600/407, 410, 424, 431, 434, 427, 437, 443, 600/459, 466, 467; 310/334; 128/897; 702/85, 702/93
See application file for complete search history.

(56) References Cited

U.S. PATENT DOCUMENTS

| | | | |
|---|---|---|---|
| 4,290,663 A | | 9/1981 | Fowler et al. |
| 5,391,199 A | | 2/1995 | Ben-Haim |
| 5,443,489 A | | 8/1995 | Ben-Haim |
| 5,515,853 A | * | 5/1996 | Smith et al. ............... 600/437 |
| 5,558,091 A | | 9/1996 | Acker et al. |
| 5,785,658 A | * | 7/1998 | Benaron et al. ........... 600/473 |
| 5,807,261 A | * | 9/1998 | Benaron et al. ........... 600/473 |
| 5,868,664 A | | 2/1999 | Speier et al. |
| 5,944,022 A | | 8/1999 | Nardella et al. |
| 5,983,126 A | | 11/1999 | Wittkampf |
| 6,019,725 A | * | 2/2000 | Vesely et al. .............. 600/447 |
| 6,080,101 A | | 6/2000 | Tatsuno et al. |
| 6,172,499 B1 | | 1/2001 | Ashe |
| 6,177,792 B1 | | 1/2001 | Govari et al. |

(Continued)

FOREIGN PATENT DOCUMENTS

EP  0571225 A  11/1993

(Continued)

OTHER PUBLICATIONS

Pending U.S. Appl. No. 11/030,937, Biosense Webster, Inc.

(Continued)

*Primary Examiner*—Brian Casler
*Assistant Examiner*—Joel M Lamprecht
(74) *Attorney, Agent, or Firm*—Louis J. Capezzuto (57) ABSTRACT

A probe for insertion into the body of a subject includes a sensor, a first microcircuit, which stores first calibration data with respect to the sensor, and a first connector at the proximal end of the probe. A probe adapter includes a second connector, which mates with the first connector, a signal processing circuit, which is processes the sensor signal, and a second microcircuit, which stores second calibration data with respect to the signal processing circuit. A microcontroller in the adapter receives the first and second calibration data and computes combined calibration data. The adapter includes a third connector, which mates with a fourth connector on a console. The console includes signal analysis circuitry, which analyzes the processed signal using the combined calibration data provided by the probe adapter.

16 Claims, 4 Drawing Sheets

U.S. PATENT DOCUMENTS

| | | | |
|---|---|---|---|
| 6,246,898 B1 * | 6/2001 | Vesely et al. | 600/424 |
| 6,266,551 B1 | 7/2001 | Osadchy et al. | |
| 6,370,411 B1 | 4/2002 | Osadchy et al. | |
| 6,456,864 B1 | 9/2002 | Swanson et al. | |
| 6,626,902 B1 * | 9/2003 | Kucharczyk et al. | 606/41 |
| 6,690,963 B2 | 2/2004 | Ben-Haim et al. | |
| 6,711,429 B1 * | 3/2004 | Gilboa et al. | 600/407 |
| 6,774,624 B2 * | 8/2004 | Anderson et al. | 324/207.17 |
| 6,788,967 B2 | 9/2004 | Ben-Haim et al. | |
| 6,980,921 B2 * | 12/2005 | Anderson et al. | 702/150 |
| 7,090,639 B2 * | 8/2006 | Govari | 600/437 |
| 2004/0254458 A1 | 12/2004 | Govari | |
| 2007/0185397 A1 | 8/2007 | Govari et al. | |

FOREIGN PATENT DOCUMENTS

| | | | |
|---|---|---|---|
| WO | WO 03/101534 A1 | 12/2003 | |

OTHER PUBLICATIONS

EP Search Report; EP Application No. 07 25 0514 dated Jun. 18, 2007.

EP Search Report #EP 07 25 0514 dated May 14, 2007.

EP Search Report #EP 09 25 1760 dated Sep. 11, 2009.

* cited by examiner

TWO-STAGE CALIBRATION OF MEDICAL PROBES

FIELD OF THE INVENTION

The present invention relates generally to invasive systems for medical diagnosis and treatment, and specifically to calibration of probes and sensors that are used in such systems.

BACKGROUND OF THE INVENTION

Tracking the position of probes within the body is required for many medical procedures. For example, various systems have been developed for determining the position coordinates (location and/or orientation) of an object in the body based on magnetic field sensing. These systems use sensors affixed to the object to measure the relative strengths of externally-generated magnetic fields and to derive from these measurements the position of the object. (The term "position" as used in the present patent application and in the claims refers to any set of spatial coordinates, including either location coordinates, angular orientation coordinates, or both.) Methods for magnetic-based position sensing are disclosed, for example, in U.S. Pat. Nos. 5,391,199, 5,443,489, and 6,788,967 to Ben-Haim, in U.S. Pat. No. 6,690,963 to Ben-Haim, et al., in U.S. Pat. No. 5,558,091 to Acker et al., in U.S. Pat. No. 6,172,499 to Ashe, and in U.S. Pat. No. 6,177,792 to Govari, all of whose disclosures are incorporated herein by reference.

When accurate position measurements are required, the probe may be calibrated in advance. An exemplary calibration process is described in U.S. Pat. No. 6,266,551 to Osadchy et al., whose disclosure is incorporated herein by reference. In the embodiments described in this patent, a device used to determine the location and orientation of a catheter inside the body comprises a plurality of coils adjacent to the distal end of the catheter. The catheter further comprises an electronic microcircuit adjacent to the proximal end of the catheter, which stores information relating to the calibration of the device. The microcircuit comprises a read/write memory component, such as an EEPROM, EPROM, PROM, Flash ROM or non-volatile RAM, and the information is stored in digital form. The calibration information includes data relating to the relative displacement of the distal tip of the catheter from the coils. The calibration information may also include data relating to deviation of the coils from orthogonality, or data relating to the respective gains of the coils, or a combination of these data.

U.S. Pat. No. 6,370,411 to Osadchy et al., whose disclosure is incorporated herein by reference, describes a catheter assembly for connection to a control console. The catheter assembly comprises two parts: a catheter of minimal complexity which is inserted into a patient's body, and a connection cable which connects between the proximal end of the catheter and the console. The catheter comprises a microcircuit which may carry calibration data that is specific to the catheter. The cable comprises an access circuit, which receives the information from the catheter and passes it in a suitable form to the console. Preferably, the cable operates with all catheters of a specific model or type, and therefore when a catheter is replaced, there is no need to replace the cable. The cable comprises an additional microcircuit in which information characteristic of one or more models of catheters associated with the cable is stored. The additional microcircuit may also include calibration information for the access circuit and amplifiers within the cable. The calibration information of the amplifiers may include, for example, their zero-gain, DC offset and linearity.

SUMMARY OF THE INVENTION

Embodiments of the present invention provide convenient methods for generating, storing and computing calibration information with respect to an invasive medical probe.

In disclosed embodiments, the probe connects via a suitable mating connector to an adapter, which in turn connects, via another mating connector, to a console. The probe comprises a sensor and a probe microcircuit, which stores sensor calibration data. The adapter comprises a signal processing circuit for processing a signal that is output by the sensor. The adapter comprises its own microcircuit, which stores calibration data with respect to the signal processing circuit. A microcontroller in the adapter computes combined calibration data based on the data from both of the microcircuits. Signal analysis circuitry in the console receives the processed signal and analyzes this signal using the combined calibration data provided by the probe adapter.

In an exemplary embodiment, the sensor outputs a position signal, and the signal processing circuit comprises an amplifier, which amplifies the position signal. The console uses the combined calibration data to compute accurate position coordinates of the probe, corrected for deviations due both to the sensor and to the amplifier. The adapter is made to be compatible—in terms of both hardware and software configuration—with legacy probes that comprise both sensor and amplifier and have only a single microcircuit with overall calibration data for the catheter. The console may thus be used, without hardware or software modification, both with such legacy probes and with probes that connect to the console through the adapter.

There is therefore provided, in accordance with an embodiment of the present invention, medical apparatus, including:

a probe, having a proximal end and a distal end, which is adapted for insertion into the body of a subject, the probe including a sensor, which outputs a sensor signal; a first microcircuit, which stores first calibration data with respect to the sensor; and a first connector at the proximal end of the probe, electrically coupled at least to the sensor;

a probe adapter, including a second connector, which is arranged to mate with the first connector; a signal processing circuit, which is coupled to process the sensor signal so as to output a processed signal; a second microcircuit, which stores second calibration data with respect to the signal processing circuit; a microcontroller, which is arranged to receive the first and second calibration data from the first and second microcircuits, respectively, and to compute combined calibration data based on the first and second calibration data; and a third connector, electrically coupled at least to the signal processing circuit; and a console, including a fourth connector, which is arranged to mate with the third connector; and signal analysis circuitry, which is coupled to receive at least the processed signal from the fourth connector and is arranged to analyze the processed signal using the combined calibration data provided by the probe adapter.

In a some embodiments, the sensor includes a position sensor, and the signal analysis circuitry is operative to determine coordinates of the distal end of the probe by analyzing the processed signal. In one embodiment, the position sensor is operative to generate the sensor signal responsively to a magnetic field applied externally to the body.

In a disclosed embodiment, the probe includes a catheter for insertion into a heart of the subject.

In some embodiments, the probe is a first type of probe, and the processed signal is a first processed signal, and the console is further operable in conjunction with a second type of probe, which is adapted to mate with the fourth connector and to convey at least a second processed signal to the fourth connector, and which includes a memory circuit, which stores third calibration data in a predetermined address space, which is accessed by the signal analysis circuitry in analyzing the second processed signal, and the microcontroller is operative to place the combined calibration data in the predetermined address space for reading by the processing circuitry. Typically, the console is operable in conjunction with both of the first and second types of probe without hardware or software modification according to probe type.

In one embodiment, the first calibration data are indicative of a sensitivity of the sensor and of a phase deviation introduced by the probe, and the signal processing circuit includes an amplifier, and the second calibration data are indicative of a gain of the amplifier and a second phase deviation introduced by the amplifier.

Typically, at least the first and second connectors include shielding against magnetic interference.

There is also provided, in accordance with an embodiment of the present invention, a method for performing an invasive medical procedure, including:

providing a probe, having a proximal end and a distal end, which includes a sensor, which outputs a sensor signal, a first microcircuit, which stores first calibration data with respect to the sensor, and a first connector at the proximal end of the probe, electrically coupled at least to the sensor;

connecting the first connector of the probe to a second connector of a probe adapter, which includes a signal processing circuit, which is coupled to process the sensor signal so as to output a processed signal, and a second microcircuit, which stores second calibration data with respect to the signal processing circuit, and a third connector, electrically coupled at least to the signal processing circuit;

using a microcontroller in the adapter, reading the first and second calibration data from the first and second microcircuits, respectively, and computing combined calibration data based on the first and second calibration data;

connecting the third connector of the adapter to a fourth connector of a console, which includes signal analysis circuitry;

inserting the probe into a body of a subject; and using the signal analysis circuitry, receiving via the fourth connector at least the processed signal from the adapter and analyzing the processed signal using the combined calibration data provided by the probe adapter while the probe is in the body.

The present invention will be more fully understood from the following detailed description of the embodiments thereof, taken together with the drawings in which:

DETAILED DESCRIPTION OF EMBODIMENTS

Figure 1:
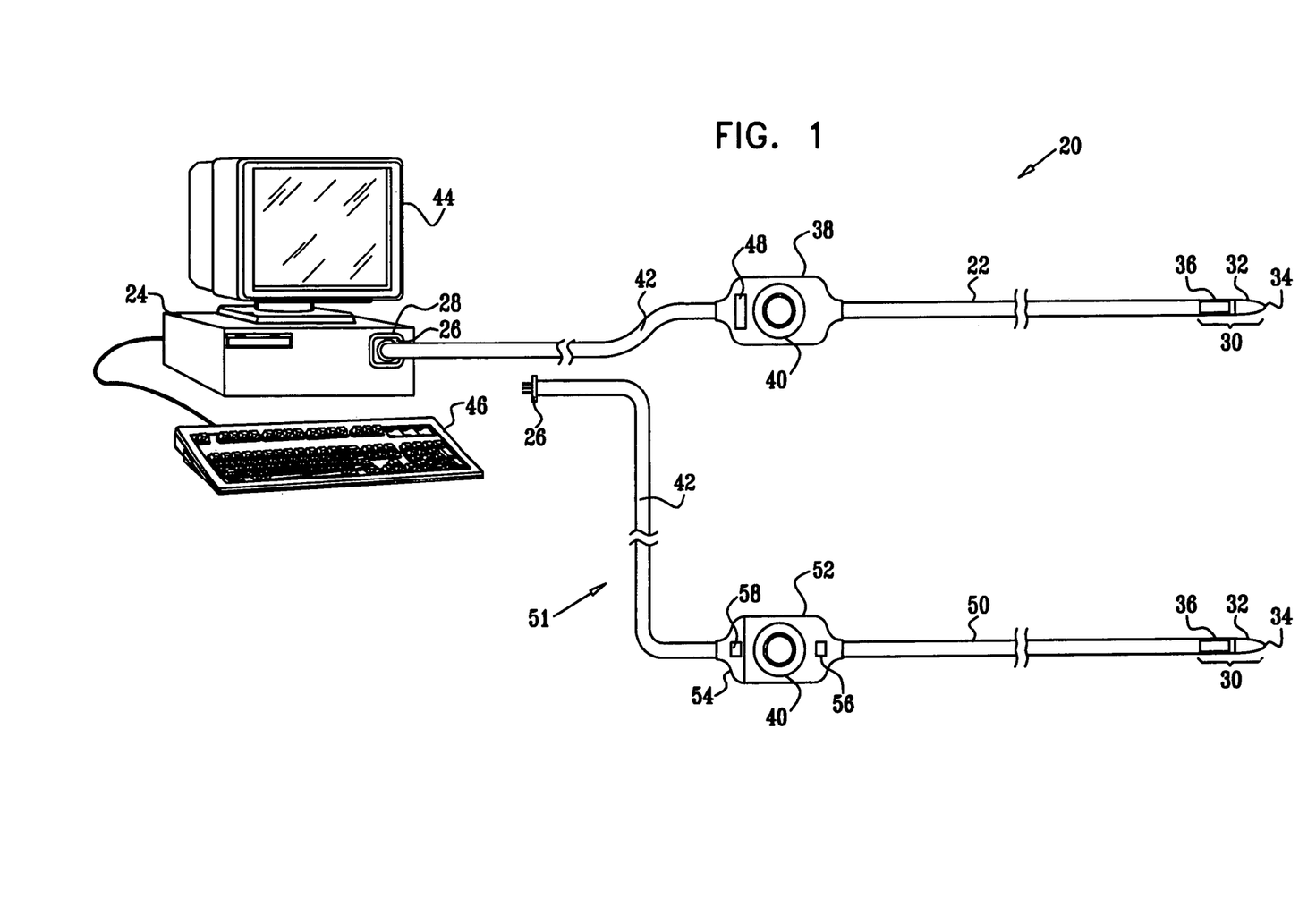
FIG. 1 is a schematic, pictorial illustration of a catheter-based medical system, in accordance with an embodiment of the present invention.

FIG. 1 is a schematic, pictorial illustration of a system 20 for cardiac catheterization, in accordance with an embodiment of the present invention. System 20 may be based, for example, on the CARTO™ system, produced by Biosense Webster Inc. (Diamond Bar, Calif.). This system comprises an invasive probe in the form of a catheter 22 and a control console 24. The catheter is typically provided to users as a disposable unit, with a connector 26, typically a plug, that mates with a corresponding connector 28, typically a receptacle, on the console. In the context of the present patent application and in the claims, the term "connector" is used in the conventional sense, to mean any sort of electrical plug or similar device that can be readily connected and disconnected in the field without technical operations such as soldering or crimping.

Catheter 22 comprises an insertion tube whose distal end 30 is designed to be passed through the vascular system and into a chamber of the heart. Typically, the distal end of the catheter comprises a functional element 32 near a distal tip 34 of the catheter for performing therapeutic and/or diagnostic functions. For example, element 32 may comprise an electrode or an ultrasound transducer.

Catheter 22 also contains a position sensor 36, which is used in determining position coordinates of distal end 30. In the CARTO system, the position sensor comprises three coils, which output signals in response to an externally-applied magnetic field. These signals are amplified by a signal processing circuit 48 in the catheter. Typically, circuit 48 is located for convenience in a handle 38 of the catheter, which also includes controls 40 for steering the catheter. The amplified signals that are output by circuit 48 pass through a cable 42 to console 24, via connectors 26 and 28. The console processes the signals to determine the coordinates of distal tip 34 and displays the result on a user interface screen 44. The user may interact with the console by means of a user input device 46, such as a keyboard. Further details of the theory and operation of magnetic position sensing systems of this type are provided in the patents cited in the Background of the Invention.

Signal processing circuit 48, cable 42 and connector 26 are costly components. In order to reduce the cost of the disposable part of system 20, an alternative catheter 50 is produced so as to permit these components to be reused over multiple procedures without sterilization. Catheter 50 comprises a connector 52 that mates with a corresponding connector 54 of an adapter 51. The catheter comprises a termination circuit 56, whose functions are described hereinbelow. Adapter 51 comprises signal processing circuitry 58 for amplifying the signals from sensor 36, as well as cable 42 and connector 26. This latter connector is plug-compatible with connector 28, so that catheter 50 (in conjunction with adapter 51) may be used interchangeably with catheter 22 in system 20. Typically, catheter 50 is a single-use device, while adapter 51 is reusable. In the embodiment shown in FIG. 1, connectors 52 and 54 are mechanically configured to form a sort of "split handle," but other mechanical configurations may also be used to achieve the same electrical functionality. For example, in one alternative embodiment, some or all of circuitry 58 is located in or near connector 26.

Figure 2A:
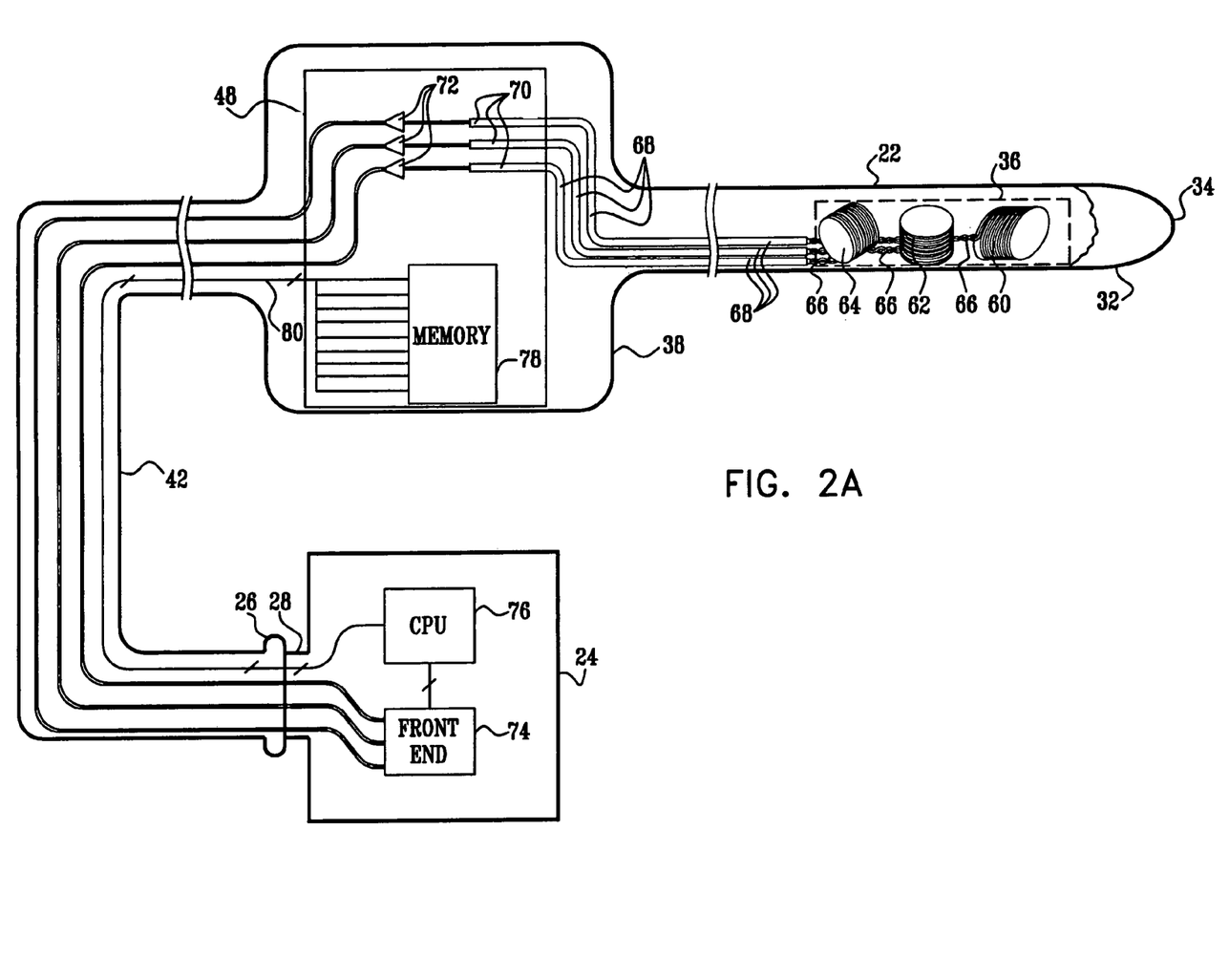
FIGS. 2A and 2B are block diagrams that schematically show circuitry used in catheters and in a console in the system of FIG. 1, in accordance with an embodiment of the present invention.

FIG. 2A is a block diagram that schematically shows details of catheter 22 and console 24, in accordance with an embodiment of the present invention. Sensor 36 comprises three non-concentric coils 60, 62 and 64, which are aligned along mutually-orthogonal axes. Coil wires 66 are connected via cables 68 to amplifiers 72 in signal processing circuit 48. Typically, cable shields 70 are grounded to a suitable ground connection (not shown) in circuit 48. The amplified signals produced by amplifiers 72 pass through cable 42, via connectors 26 and 28, to a front end circuit 74 in console 24. The front end circuit typically filters and digitizes the signals and passes the resulting digital samples to a central processing unit (CPU) 76, which processes the samples in order to compute the location and orientation coordinates of distal tip 34.

Catheter 22 is calibrated in the factory in order to determine the combined sensitivity and phase offset of coils 60, 62, 64 and amplifiers 72, as well as the exact location and angular skew of the coils relative to the distal tip of the catheter. The calibration data are then stored in a microcircuit memory 78, such as an electrically-erasable programmable read-only memory (EEPROM) in handle 38. When the catheter is subsequently connected to console 24 for clinical use, CPU 76 reads the calibration data from memory 78 via a bus 80 passing through cable 42. Typically, the calibration data are arranged in a predetermined format, and the CPU is programmed to read the data from a certain address or range of addresses in the memory. The CPU uses the calibration data in determining accurate position coordinates of the catheter tip based on the sensor signals. The calibration process and the use of memory 78 to store the calibration parameters are described in detail in the above-mentioned U.S. Pat. No. 6,266,551.

Figure 2B:
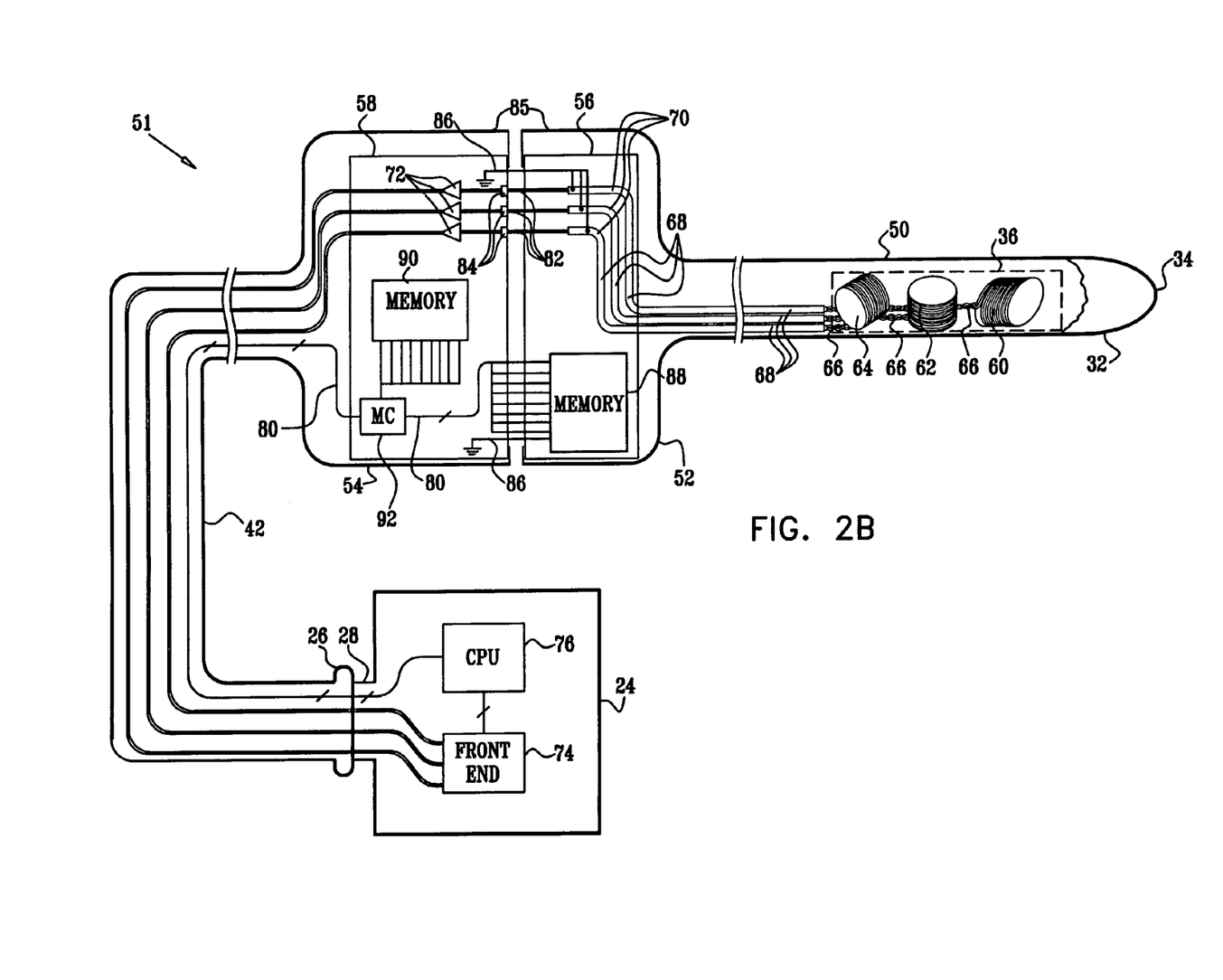

FIG. 2B is a block diagram that schematically shows details of catheter 50, adapter 51 and console 24, in accordance with an embodiment of the present invention. Sensor 36 in catheter 50 is identical to that in catheter 22, and both catheters work with the same console 24, as noted above. Cables 68 in catheter 50 connect to connector pins 82 of connector 52. These pins mate with receptacles 84 of connector 54. Connectors 52 and 54 typically also comprise ground connections 86 for grounding the circuits in catheter 50. Typically, connectors 52 and 54 comprise magnetic shielding 85, using μ-metal, for example, to reduce magnetic interference with the weak signals on pins 82.

Both sensor coils 60, 62, 64 in catheter 50 and amplifiers 72 in adapter 51 contribute to the overall sensitivity and phase offset of the system. Since the adapter may be used with many different catheters, and a given catheter may be used with any adapter, the sensor coils and the amplifiers are calibrated separately. In other words, separate calibration data must be determined for each catheter and for each adapter. The appropriate calibration data for the given catheter and the given adapter are then combined when the catheter and adapter are used together in the field in order to determine the correct overall calibration factors to be applied by CPU 76 to the amplified sensor signals.

If console 24 was originally designed to operate with unitary catheters (such as catheter 22, as shown in the preceding figures), however, then the console may be wired and programmed to receive only one set of calibration factors from the memory in the catheter. As noted above, in legacy catheters these calibration factors relate to the combined characteristics of the sensor coils and amplifiers. The console is not capable of receiving and using separate catheter and adapter calibration factors.

To address this problem, two memories 88 and 90 are used to contain the calibration data: memory 88 in catheter 50 and memory 90 in adapter 51. These memories may comprise EEPROM chips or any other suitable type of non-volatile memory, such as EPROM or Flash memory. Catheter memory 88 contains calibration data with respect to sensor coils 60, 62, 64. Adapter memory 90 contains calibration data relating to circuit 58, and particularly to the characteristics of amplifiers 72.

A microcontroller 92 in adapter 51 reads the calibration data from both of memories 88 and 90 and computes a combined set of calibration factors. The microcontroller then provides the combined calibration factors to the console in a manner that emulates the legacy interface of memory 78 in catheter 22 (FIG. 2A). For example, the microcontroller may write the combined calibration factors to the same address range in memory 90 as CPU 76 is programmed to access for this purpose, in the same format as is used for the calibration factors in memory 78. Therefore, no modification is required to console 24 to enable it to receive and apply the calibration factors computed by microcontroller 92.

Although sensor 36 is described above as a magnetic position sensor, the system configuration and methods described herein may also be applied in conjunction with other types of position sensors, such as ultrasonic and impedance-based position sensors. In impedance-based systems, for example impedance is measured between electrodes affixed to the catheter and electrodes placed on the body surface, and location coordinates are derived from the impedance measurements. Methods for impedance-based position sensing are disclosed, for example, in U.S. Pat. No. 5,983,126 to Wittkampf, in U.S. Pat. No. 6,456,864 to Swanson, and in U.S. Pat. No. 5,944,022 to Nardella, as well as in U.S. patent application Ser. No. 11/030,934 filed on Jan. 7, 2005, all of whose disclosures are incorporated herein by reference.

Furthermore, although the embodiments describe herein relate specifically to calibration and operation of a position sensor, memories 88 and 90 and microcontroller 92 may similarly be used in calibrating sensors of other types used in catheter 50 or in other sorts of probes. For example, assuming functional element 32 to be a sensor, such as a sensing electrode, a chemical sensor, a temperature sensor, a pressure sensor or an ultrasonic transducer, memory 88 may contain calibration data with respect to this sensor. Additionally or alternatively, the memory may contain calibration data with respect to an ultrasonic imaging transducer that is used in conjunction with a position sensor, as described, for example, in U.S. patent application Ser. No. 10/447,940, to Govari (published as US 2004/0254458 A1), whose disclosure is incorporated herein by reference.

Memories 88 and 90 may also be used to hold access control parameters, as described in the above-mentioned U.S. Pat. No. 6,266,551. These parameters may include, for example, an identification code, or a use counter or expiration time. Microcontroller 92 may read and process parameters that are stored in memories 88 and 90 and provide the result to CPU 76. The CPU may then prevent operation of system 20 if the parameters indicate that an improper or, expired catheter or adapter has been connected to the console.

Figure 3:
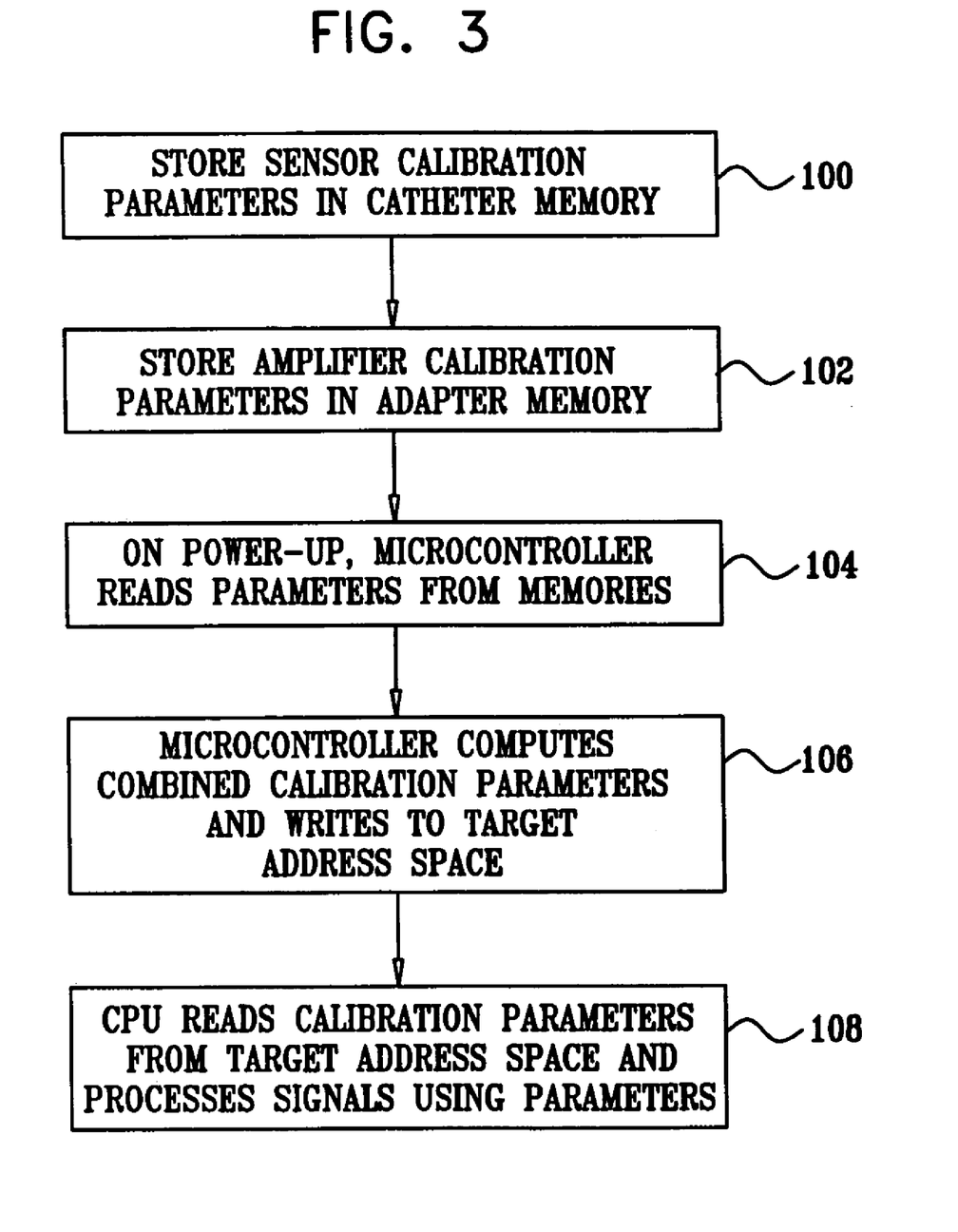
FIG. 3 is a flow chart that schematically illustrates a method for catheter calibration, in accordance with an embodiment of the present invention.

FIG. 3 is a flow chart that schematically illustrates a method for calibrating and processing signals produced by catheter 50, in accordance with an embodiment of the present invention. Sensor 36 in catheter 50 is calibrated using a suitable calibration setup, at a sensor calibration step 100. A jig and procedures that may be for this purpose are described in the above-mentioned U.S. Pat. No. 6,266,551. The sensor calibration parameters typically include the sensitivity and phase shift $S_{ij}^{sensor}$, $\Phi_{ij}^{sensor}$ of each of coils 60, 62 and 64, measured relative to an externally-applied magnetic field of known amplitude and phase. The calibration parameters may also include the spatial offset of each of the coils relative to distal tip 34 of catheter 50, as well as the deviation of the coil axes from orthogonality. The calibration data are stored in memory 88.

Amplifiers 72 in adapter 51 are calibrated, as well, at an adapter calibration step 102. For this purpose, test signals may be applied to the inputs of the amplifiers (via connector 54, for example), and the amplifier outputs may be measured in order to determine the amplifier gains and phase shifts $A_{ij}^n$, $\phi_{ij}^n$. These results are stored in memory 90.

When connectors 52 and 54 and coupled together, and system 20 is powered up, microcontroller 92 reads the calibration parameters from memories 88 and 90, at a start-up step 104. The microcontroller then computes combined calibration parameters for the catheter and adapter together, at a combined parameter computation step 106. For example, the microcontroller may multiply each of the sensor coil sensitivity values by the gain of the corresponding amplifier to give a combined sensitivity value, and may sum the sensor phase shift with the phase shift of the amplifier to give a combined phase shift value. Alternatively, more complex computation algorithms may be applied to combine the parameters.

Microcontroller 92 writes the combined calibration parameter values to the appropriate target address space where CPU 76 expects to find the calibration parameters. For example, a range of addresses in memory 90 may be left available for this purpose. After writing the parameters to this range, microcontroller routes the control and data lines of memory 90 so as to enable CPU to read the parameters from the memory via bus 80. For this purpose, the microcontroller may set internal switches within the microcontroller or set external switches (not shown) in circuit 58. Alternatively, the microcontroller may save the combined calibration parameter values in an internal memory, which is mapped to the appropriate target address space of CPU 76, and may emulate the operation of memory 78 when the CPU attempts to read the values.

CPU 76 reads the combined calibration parameter values from adapter 51, at a parameter reading step 108. The CPU then applies these values in processing the signals that it receives from catheter 50. Operation of system 20 proceeds in an identical manner regardless of whether catheter 22 or catheter 50 is used.

Although the embodiments described above relate specifically to certain types of cardiac catheters, the principles of the present invention may similarly be applied to invasive medical probes and systems of other types. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Medical apparatus comprising:
a probe, having a proximal end and a distal end, which is adapted for insertion into the body of a subject, said probe comprising:
   a sensor, which outputs a sensor signal;
   a first microcircuit, which stores first calibration data with respect to the sensor; and
   a first connector at the proximal end of the probe, electrically coupled at least to the sensor;
a probe adapter configured to be detachably connected to the probe, said probe adapter comprising:
   a second connector, which is arranged to mate with the first connector of the probe;
   a signal processing circuit, which is coupled to process the sensor signal so as to output a processed signal;
   a second microcircuit, which stores second calibration data with respect to the signal processing circuit;
   a microcontroller, which is arranged to receive the first calibration data from the first microcircuit of the probe and second calibration data from second microcircuit of the probe adapter, respectively, and to compute combined calibration data based on the first calibration data and the second calibration data; and
   a third connector, electrically coupled at least to the signal processing circuit; and
a console, comprising:
   a fourth connector, which is arranged to mate with the third connector; and
   signal analysis circuitry, which is coupled to receive at least the processed signal from the fourth connector and is arranged to analyze the processed signal using the combined calibration data provided by the probe adapter.

2. The apparatus according to claim 1, wherein the sensor comprises a position sensor, and wherein the signal analysis circuitry is operative to determine coordinates of the distal end of the probe by analyzing the processed signal.

3. The apparatus according to claim 2, wherein the position sensor is operative to generate the sensor signal responsively to a magnetic field applied externally to the body.

4. The apparatus according to claim 1, wherein the probe comprises a catheter for insertion into a heart of the subject.

5. The apparatus according to claim 1, wherein the probe is a first type of probe, and the processed signal is a first processed signal, and
wherein the console is further operable in conjunction with a second type of probe, which is adapted to mate with the fourth connector and to convey at least a second processed signal to the fourth connector, and which includes a memory circuit, which stores third calibration data in a predetermined address space, which is accessed by the signal analysis circuitry in analyzing the second processed signal, and
wherein the microcontroller is operative to place the combined calibration data in the predetermined address space for reading by the processing circuitry.

6. The apparatus according to claim 5, wherein the console is operable in conjunction with both of the first and second types of probe without hardware or software modification according to probe type.

7. The apparatus according to claim 1, wherein the first calibration data are indicative of a sensitivity of the sensor and of a phase deviation introduced by the probe, and wherein the signal processing circuit comprises an amplifier, and the second calibration data are indicative of a gain of the amplifier and a second phase deviation introduced by the amplifier.

8. The apparatus according to claim 1, wherein at least the first and second connectors comprise shielding against magnetic interference.

9. A method for performing an invasive medical procedure, comprising:
providing a probe which is a disposable single-use device, having a proximal end and a distal end, which comprises a sensor, which outputs a sensor signal, a first microcircuit, which stores first calibration data with respect to the sensor, and a first connector at, the proximal end of the probe, electrically coupled at least to the sensor;
detachably connecting the first connector of the probe to a second connector of a probe adapter, the probe adapter being reusable and which comprises a signal processing circuit, which is coupled to process the sensor signal so as to output a processed signal, and a second microcircuit, which stores second calibration data with respect to the signal processing circuit, and a third connector, electrically coupled at least to the signal processing circuit of the probe adapter;

using a microcontroller in the probe adapter, reading the first calibration data from the first microcircuit of the probe and second calibration data from the second microcircuit of the probe adapter, respectively, and computing a combined calibration data based on the first and second calibration data;

connecting the third connector of the probe adapter to a fourth connector of a console, which comprises signal analysis circuitry;

inserting the probe into a body of a subject; and using the signal analysis circuitry, receiving via the fourth connector at least the processed signal from the probe adapter and analyzing the processed signal using the combined calibration data provided by the probe adapter while the probe is in the body.

10. The method according to claim 9, wherein the sensor comprises a position sensor, and wherein analyzing the processed signal comprises determining coordinates of the distal end of the probe.

11. The method according to claim 10, wherein the position sensor is operative to generate the sensor signal responsively to a magnetic field applied externally to the body.

12. The method according to claim 9, wherein the probe comprises a catheter for insertion into a heart of the subject.

13. The method according to claim 9, wherein the probe is a first type of probe, and the processed signal is a first processed signal, and wherein the console is further operable in conjunction with a second type of probe, which is adapted to mate with the fourth connector and to convey at least a second processed signal to the fourth connector, and which includes a memory circuit, which stores third calibration data in a predetermined address space, which is accessed by the signal analysis circuitry in analyzing the second processed signal, and wherein computing the combined calibration data comprises placing the combined calibration data in the predetermined address space for reading by the processing circuitry.

14. The method according to claim 13, wherein the console is operable in conjunction with both of the first and second types of probe without hardware or software modification according to probe type.

15. The method according to claim 9, wherein the first calibration data are indicative of a sensitivity of the sensor and of a phase deviation introduced by the probe, and wherein the signal processing circuit comprises an amplifier, and the second calibration data are indicative of a gain of the amplifier and a second phase deviation introduced by the amplifier.

16. The method according to claim 9, wherein connecting the first connector to the second connector comprises shielding at least the first and second connectors against magnetic interference.

* * * * *